United States Patent [19]

Lee

[11] Patent Number: 5,257,101
[45] Date of Patent: Oct. 26, 1993

[54] APPARATUS AND METHOD FOR SELECTING A LOG ORIENTATION AND PATTERN FOR SAWING

[75] Inventor: Samuel C. Lee, Norman, Okla.

[73] Assignee: Board of Regents of the University of OK, Norman, Okla.

[21] Appl. No.: 891,350

[22] Filed: Jun. 1, 1992

[51] Int. Cl.$^5$ .............................................. H04N 7/18
[52] U.S. Cl. ................................... 358/101; 358/903; 364/468; 382/8
[58] Field of Search ................. 358/93, 101, 106, 107, 358/903; 382/8; 364/468, 560

[56] References Cited

U.S. PATENT DOCUMENTS

| | | | |
|---|---|---|---|
| 4,152,767 | 5/1979 | Laliotis | 364/560 |
| 4,188,544 | 2/1980 | Chasson | 358/107 |
| 4,879,659 | 11/1989 | Bowlin | 364/468 |
| 4,879,752 | 11/1989 | Aune | 358/106 |
| 4,947,909 | 8/1990 | Stroud | 364/561 |

OTHER PUBLICATIONS

"Lumber Values From Computerized Simulation of Hardwood Log Sawing," by D. B. Richards, W. K. Adkins, H. Hallock and E. H. Bulgrin, Res. Pap. FPL-356 USDA Forest Sev. Forest Prod. Lab., Jan. 1980, pp. 1-7.
"Simulation of Hardwood Log Sawing," by D. B. Richards, W. K. Adkins, H. Hallock and E. H. Bulgrin, Res. Pap. FPL-355 USDA Forest Serv. Forest Prod. Lab., 1979, pp. 1-10.
"Programs for Computer Simulation of Hardwood Log Sawing," by W. K. Adkins, D. B. Richards, D. W. Lewis and E. H. Bulgrin, Res. Pap. FPL-357 USDA Forest Serv. Forest Prod. Lab., 1980, pp. 1-9.
"A Simulation Model for Log Yield Study," by Jordan A. Tsolakides, *Forest Products Journal*, Jul. 1969, vol. 19, No. 7, pp. 21-26.
"Value Yield From Simulated Hardwood Log Sawing," by D. B. Richards *Forest Products Journal*, Dec. 197, vol. 27, No. 12, pp. 47-50.
"Application of Automatic Image Analysis to Wood Science," by Charles W. McMillin, Wood Science, vol. 14, No. 3, Jan. 1982, pp. 97-105.
"Simulated Sawing With a Chipping Headrig," by Francis G. Wagner, Jr., *Forest Products Journal*, Oct. 1973, vol. 25, No. 10, pp. 24-28.
"Sawing Pattern Effect on the Yield of Lumber and Furniture Components from Medium and Low Grade Maple Logs," by S. M. Pnevmaticos and D. B. Bousquet, *Forest Products Journal*, Mar. 1972, vol. 22, No. 3, pp. 34-41.
"Influence of Sawing Methods on Lumber Grade Yield from Yellow-Poplar," by R. K. Peter, *Forest Products Journal*, Nov. 1967, vol. 17, No. 11, pp. 19-24.

*Primary Examiner*—Howard W. Britton
*Attorney, Agent, or Firm*—Dunlap, Codding & Lee

[57] ABSTRACT

An apparatus for optically scanning a log and selecting an optimal log orientation for sawing the log into lumber. The apparatus includes a log holder, a camera, and a computer system connected to the camera. The log holder comprises a set of rollers to facilitate rotation of the log and a red background to provide visual contrast with the log. Fluorescent lights directed toward the log are secured to a frame and directed toward the log to provide uniform lighting for scanning the log. The camera is mounted on the frame for movement parallel with the length of the log to obtain optical images of the entire log, one section at a time. The log is rotated 180° in each section in order to scan the entire outer surface of the log. The computer system comprises an interface for converting the optical images into computer images. The computer system also includes software for generating a computer model of the log and its knots, for simulating the sawing of the log into boards, for grading the boards, and for assigning a value yield to the boards. The computer system determines a value yield for boards cut from the log according to a predetermined sawing pattern at 360 angles of log orientation and selects one angle as an optimal cutting angle. An optimal sawing pattern may be selected as well by determining an optimal value yield for several sawing patterns and selecting the sawing pattern with the highest value yield.

17 Claims, 5 Drawing Sheets
Microfiche Appendix Included
(1 Microfiche, 37 Pages)

APPARATUS AND METHOD FOR SELECTING A LOG ORIENTATION AND PATTERN FOR SAWING

MICROFICHE APPENDIX

This application includes a microfiche appendix of computer software listings. The microfiche appendix has a total of one microfiche and a total of 56 microfiche frames.

FIELD OF THE INVENTION

The present invention relates to analyzing the location, size and shape of knots in logs to be cut into lumber products and to selecting a log orientation and sawing pattern which results in graded lumber products with a high lumber value yield for the log.

SUMMARY OF THE INVENTION

In order for the lumber industry to lower the tree cutting rate, various techniques for improving the value yield of a log have been proposed. One such technique is to scan the log by some nondestructive means, such as X-ray, microwave or nuclear magnetic resonance imaging, to determine the internal features of the log before sawing. Once the internal defects of the log are known, an optimum log breakdown strategy can be determined to increase the lumber value yield of the log.

Laser scanners, microwave scanners, nuclear magnetic scanners and computerized axial tomographic (CAT) scanners, however, are not suitable for wide use because of their high cost and potential hazard to workers. On the other hand, an optical scanner is low in cost and can be operated with minimal risk to workers.

The present invention utilizes an optical scanner to detect knots, which are the most frequently occurring defects on the outer surface of a log. The optical scanner comprises a charge-coupled device video camera mounted on a rack and directed toward a log supported on a log holder. The camera is mounted to the rack with rollers so that it is able to travel parallel to the log and obtain images of the entire length of the log. The log holder is constructed for rotation of the log about its longitudinal axis to expose the entire outer surface of the log to the camera.

The camera is connected to a computer adapted to receive the visual images of the log. The computer has software and hardware to process the camera location, the rotational position of the log and the pictures of the log to produce a three-dimensional computer model of the log with electronic images of the outer surface of the log.

The computer software performs a series of steps to distinguish knots from bark and other surface features, to model the geometry of knots inside the log from the surface images of the knots, and to select a log orientation and cutting pattern which result in a high lumber value yield for the log.

Other advantages and features of the present invention are apparent from the following detailed description when read in conjunction with the accompanying drawings and appended claims.

BRIEF DESCRIPTION OF THE DRAWINGS

FIG. 18 is a diagram illustrating the value yield of a log versus the orientation of the log in degrees.

FIG. 19 is a diagram illustrating another sawing pattern which may be be analyzed for value yield of a log.

DETAILED DESCRIPTION OF THE PREFERRED EMBODIMENTS

While a number of defects such as diseased areas, worm holes and splits may affect the grade of lumber products, the most common defects are knots. The presence of knots with diameters greater than one inch usually determines the grade of the board. The present invention utilizes an optical log scanner and a computer system to detect and model knots in a log. The computer system then analyzes predefined log orientations and sawing patterns to determine an orientation and pattern which produces a high yield value of lumber to be cut from the log.

An optical scanner creates images of only the outer surface of a log. In order for a knot to be detectable from the images of the optical scanner, the knot must appear, at least partially, on the surface of the log.

For the purposes of this disclosure, two types of knots which appear on the surface of a log are discussed. The first type of knot, the "lump knot," is defined as a knot which protrudes from the surface of the log.

The second type of knot, the "surface knot," is a knot which does not jut out from the surface of the log. The surface knot may be substantially even with the surface of the log or may form a depression in the surface of the log. As a result of the de-barking process, surface knots are a common occurrence in logs ready to be cut into lumber.

Figure 1:
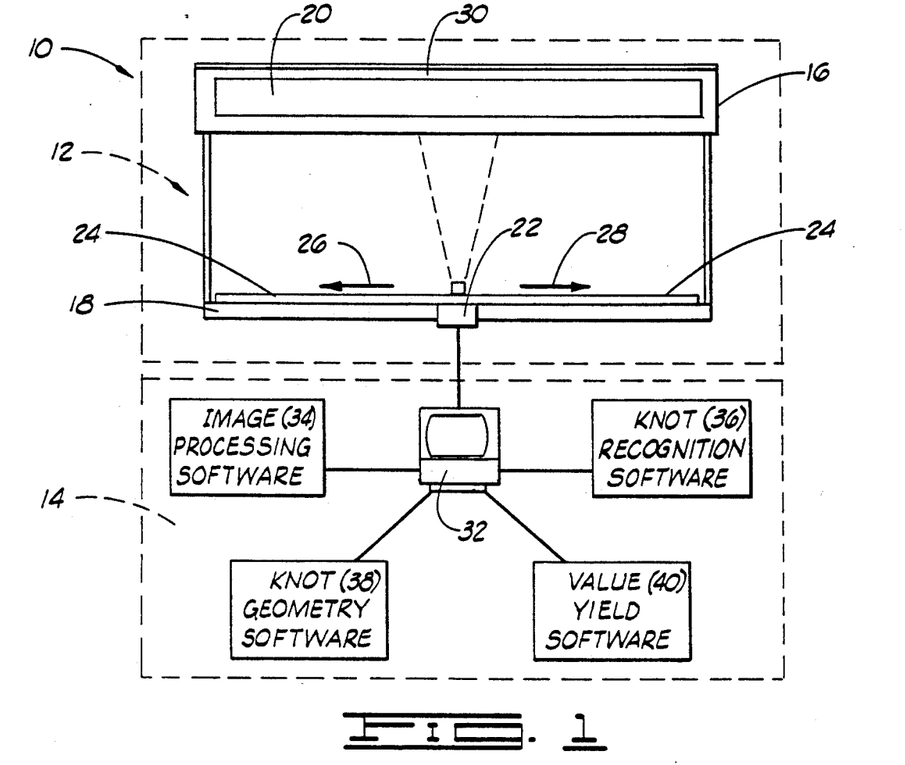
FIG. 1 is a diagrammatical view of an apparatus constructed in accordance with the present invention.

Referring to the details of FIG. 1 reference numeral 10 designates an apparatus constructed in accordance with the present invention. The apparatus 10 comprises an optical log scanner 12 connected to a computer system 14.

The optical log scanner 12 includes a log holder 16 and a mounting rack 18 which extend parallel to the length of the log holder 16. A log 20 to be scanned is positioned on the log holder 16.

A camera 22 is mounted to the rack 18 and is trained upon the log 20. A plurality of fluorescent lights, generally designated as reference number 24, are mounted to the rack 18 to illuminate the log 20.

As indicated by direction arrows 26 and 28, the camera 22 is adapted to roll along the length of the rack 18 in order to frame the entire length of the log 20, one section at a time. In FIG. 1, the section of the log 20 being framed is indicated by the broken lines extending from the camera 22 to the log 20.

A uniform background material 30 is positioned along the length of the log 20 opposite the camera 22 to provide a contrasting background for the optical scanning of the log 20.

The camera 22 in FIG. 1 is connected by an appropriate interface cable to the computer system 14. Typically, the computer system 14 comprises a conventional 386 model 20 personal computer with a professional image board having a resolution of $512 \times 256$ for image processing.

The computer system 14 also includes executable software for image processing 34, knot recognition 36, knot geometry 38 and value yield computation and analysis 40.

Figure 2:
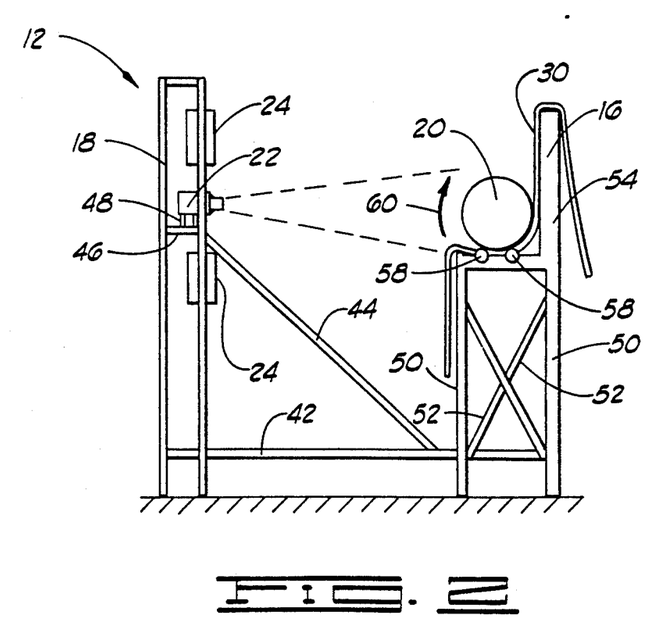
FIG. 2 is an elevational view of the optical log scanner, log holder and log of FIG. 1.

Referring now to FIG. 2, the log optical scanner 12 is described in greater detail. The mounting rack 18 is located at a predetermined distance from the log holder 16 and is supported in a stationary position by horizontal braces 42 and diagonal braces 44 on each side. The mounting rack 18 includes a shelf 46 for the camera 22. A plurality of rollers 48 are attached to the bottom of the camera 22 to facilitate movement of the camera 22 along the length of the shelf 46 to scan the entire length of the log 20.

The log holder 16, the shelf 46, and the camera lens are positioned to ensure that all sections of the log 20 will be within the camera frame and that the longitudinal axis of the log 20 is substantially centered in the camera frame throughout the length of the log 20.

A variety of charged-coupled device video cameras may be employed with the log optical scanner 12. A color camera, however, yields better results than a black-and-white camera in differentiating bark from knots in the log 20.

In order to obtain well-defined images, lights 24 are mounted to the rack 18 above and below the camera 22. Fluorescent light tubes with translucent covers may be used to provide proper illumination of the log 20. In addition, fluorescent tubes are easily arranged along the length of the rack 18 because of their elongated shape.

The log holder 16 in FIG. 2 is basically a work bench having a plurality of legs 50, braces 52, a back 54, and a horizontal surface 56 with a plurality of rollers 58 for rotating the log 20. The direction arrow 60 indicates the direction of rotation of the log 20.

It is important to mark the surface of the log 20 to designate the initial log orientation and the direction of log rotation. Such marks provide a reference on the log 20 when the log 20 is physically cut and also assist in maintaining the proper correlation between the log orientation and the images taken by the camera 22.

In a low volume application, the log 20 may be rotated manually and the camera 22 may be moved along the shelf 46 by hand. It is advantageous to provide markings on the shelf 46 for positioning the camera 22 to take images of each log section. Similarly, it is helpful to have an indication on the log holder 16 by which to position the end of the log 20 in setting up the log 20 for scanning.

In a commercial sawmill, where many logs are to be scanned, it may be desirable to provide a step-motor and drive mechanism (not shown) for rotating the log 20. The movement of the camera 22 may also be automated and controlled to stop at the proper position on the shelf 46 to take images of each log section.

In any case, it is imperative that the log 20 is scanned in sequential sections beginning with the initial log orientation for each section. In this manner, the optical images of the camera 22 are presented to the computer system 14 in order of log section and angle of log orientation within each log section.

The log holder 16 should be long enough to accommodate the longest log to be scanned and sturdy enough to support the weight of the heaviest log to be scanned. The background material 30 is disposed between the log 20 and the log holder 16 to provide good contrast between the log 20 and the background.

The color of the background material 30 is important for the separation of the log profile from the image background. Southern pine logs, for example, are nearly white in color. When they are scanned by a color vision system, each pixel of the log image taken by the system consists of three components: red, green and blue.

Because the color of the log is near white, the ratio among the three red-green-blue components is approximately $\frac{1}{3}:\frac{1}{3}:\frac{1}{3}$. From this ratio, it is apparent that any one of the three basic colors may be used for the image background for the log scanner 12.

When a pure red background is used, for example, the difference between the background and the log in the scanned image can be easily found from the ratios of the three color components. The ratio of the red background would be 1:0:0 and the ratio of the near white log would be close to $\frac{1}{3}:\frac{1}{3}:\frac{1}{3}$.

The difference in color ratios can be further amplified by using the red-to-green ratios. The red background would have a very large red-to-green ratio (1 divided by $0 = \infty$) and the log would have a relatively small red-to-green ratio ($\frac{1}{3}$ divided by $\frac{1}{3} = 1$). Using these color ratios, the original color image is converted by the image processing software 34 into a black-white or binary image of the log profile, where black is the background and white is the log.

Knot Recognition

The shape of a knot inside a log is approximately the shape of a paraboloid with its origin at the longitudinal centerline of the log. Knots generally extend angularly from the center of the log toward the outer surface of the log. At the surface of the log, knots are typically elliptical in shape.

In order to define the location, size and shape of a knot in a log, four knot parameters are determined. These four knot features are defined as follows.

Knot angular location, $\alpha_k$, is the angular location of the knot with respect to the initial log orientation $\alpha_L$.

Knot angular displacement, $\beta_k$, is the angle measured between the longitudinal centerline of the knot and the longitudinal centerline of the log.

Knot surface diameter, $d_k$, is the diameter of the knot at the outer surface of the log.

Knot longitudinal location, $z_k$, is the distance between the log's reference end, or beginning end, and the origin of the knot at the longitudinal centerline of the log.

Once these four knot parameters are determined, the knot geometry software 38 has sufficient information to generate a computer model of the knot in the log.

Profile Recognition of Lump Knots

The knot recognition software 36 may be viewed as performing two basic processes. The first process is the profile recognition of lump knots, knots protruding from the outer surface of the log 20. The second process is the pattern recognition of all knots appearing on the outer surface of the log 20.

Figure 3:
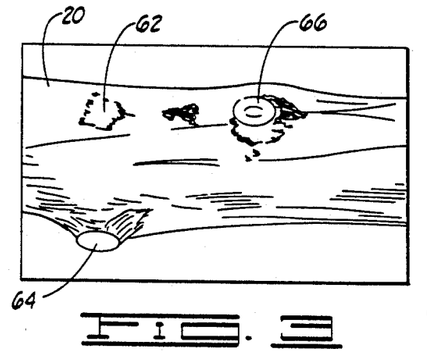
FIG. 3 is a diagram of a profile image frame of a log at an orientation angle of $\alpha_L = 0°$.

Turning first to the profile recognition of lump knots, FIGS. 3 through 6 illustrate image profiles of the same section of a log at different angles $\alpha_L$. In order of increasing angle $\alpha_L$, FIG. 3 is an image profile at the initial log orientation of $\alpha_L = 0°$, FIG. 4 corresponds to $\alpha_L = 20°$, FIG. 5 corresponds to $\alpha_L = 40°$, and FIG. 6 corresponds to $\alpha_L = 60°$.

Several lump knots appear in FIGS. 3 through 6. Three lump knots are designated by reference numerals 62, 64 and 66. Each reference number 62, 64 and 66 indicates the same lump knot in in FIGS. 3 through 6.

Figure 4:
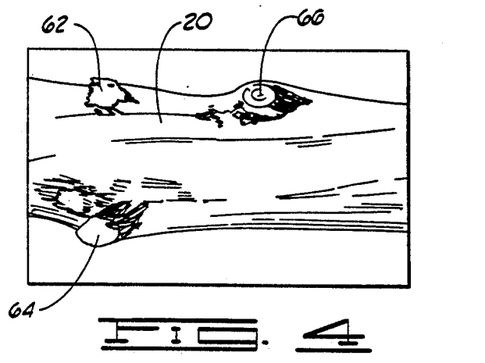
FIG. 4 is a diagram of a profile image frame of the log of FIG. 3 at an orientation angle of $\alpha_L = 20°$.
Figure 5:
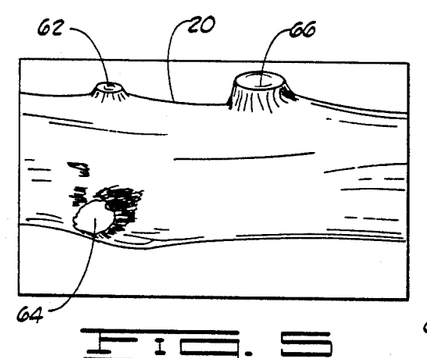
FIG. 5 is a diagram of a profile image frame of the log of FIG. 3 at an orientation angle of $\alpha_L = 40°$.
Figure 6:
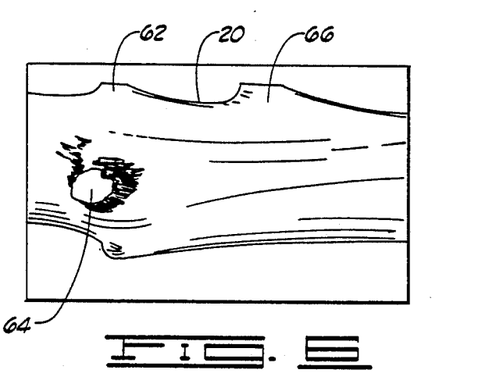
FIG. 6 is a diagram of a profile image frame of the log of FIG. 3 at an orientation angle of $\alpha_L = 60°$.

Focusing now on lump knot 66 in FIGS. 3 through 6, it is apparent that FIG. 5 shows the most prominent profile of lump knot 66. In FIGS. 3 and 4, the lump knot 66 has not yet rotated into full profile. In the profile image of FIG. 6, the lump knot 66 has rotated beyond full profile to be partially on the back side of the log 20.

The knot recognition software 36, therefore, selects the image profile of FIG. 5 to identify the location and size of lump knot 66. From the profile of FIG. 5, two of the four knot parameters for lump knot 66 may be directly determined.

Figure 7:
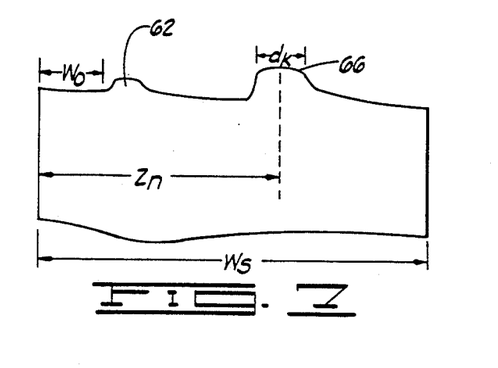
FIG. 7 is a diagram of the profile of a lump knot taken from FIG. 5, the profile image frame with the highest peak for the lump knot.

Referring now to FIG. 7, the information about lump knot 66 determined by profile recognition is described in detail. The knot surface diameter, $d_k$, is easily scaled from its dimension in the image profile for lump knot 66.

The knot angular location, $\alpha_k$, for lump knot 66 is also provided by the image profile. Because the image selected for a lump knot is a profile, the $\alpha_k$ for a lump knot is offset 90° from the log angular location, $\alpha_L$, for that particular image frame.

For example, it is known that the log orientation $\alpha_L = 40°$ in FIG. 5. Adjusting for the 90° profile offset, $\alpha_k$ for lump knot 66 is approximately (40° − 90°) or 310°.

In scanning the log, the incremental change in the angle $\alpha_L$ between each image profile is selected before the scanning begins and may be varied from one scan to the next. For the size and height of knots found on a southern pine, increments of 10° are found to yield acceptable results. For simplicity, 20° increments in the angle $\alpha_L$ are shown in FIGS. 3 through 6.

Referring once again to FIG. 7, the longitudinal distance from the beginning end of the log 20 to the center of the lump knot 66, $z_s$, is also determined from the profile image. The $z_s$ value is calculated using the formula:

$$z_s = (S_n - 1) \times (W_s - W_o) + Z_n$$

where $S_n$ = the sequential number of the scanned log section
$W_s$ = the width of each scanned log section
$W_o$ = the width of the overlap in scanned log sections
$Z_n$ = the distance within the log section from the beginning of the scanned log section to the center of the knot.

Pattern Recognition of Lump and Surface Knots

Recognition of surface knots is much more complicated than recognition of lump knots. Because of the unevenness of the log surface, pieces of bark are often left on the log after the debarking process. Strips of bark remains, resulting from the pressure applied to the bark during de-barking, frequently appear on the log surface also.

The camera lens, of course, takes images of knots, pieces of bark and bark remains on the log in addition to the wood itself. The major problem to be solved is how to distinguish knots from the wide range of other surface features on a log. Compounding the problem is the fact that the surface features of a log (knots, pieces of bark, bark remains, etc.) vary in size, shape, color, intensity and texture.

The knot recognition software 36 solves this problem by performing knot pattern recognition in two major phases: an image preprocessing phase and a pattern detection phase. In the image preprocessing phase, the binary image of the log surface is analyzed to find the image edges.

Figure 8:
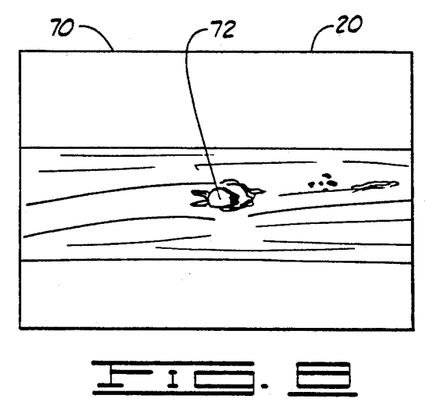
FIG. 8 is a diagram of an unaltered image frame of a surface knot.

With reference now to FIG. 8, an original optical image of a section of the log 20 is illustrated. A knot 72 appears on the surface of the log 20 in a log section designated by reference numeral 70. It should be appreciated that the knot 72 may be either a lump knot, protruding from the log 20, or a surface knot.

If the knot 72 is a lump knot, it will already have been identified by the profile recognition procedure as previously described. Even though already identified, a lump knot is subjected to pattern recognition to confirm that the protruding feature is in fact a knot.

Figure 9:
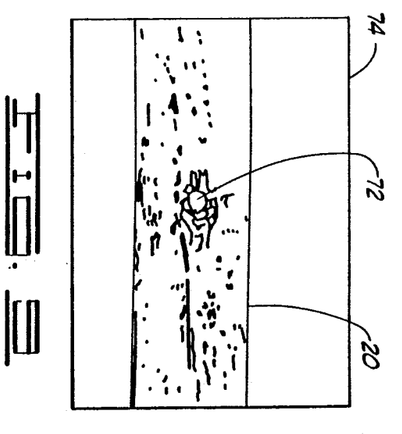
FIG. 9 is a diagram of the image frame of FIG. 8 after the application of edge detection by the computer system.

Referring now to FIG. 9, the pattern recognition software has produced a binary computer image 74 of the log section 70. In the binary image 74, each point or pixel of the image is either on or off, either black or white. Accordingly, lighter areas are made white and darker areas are made black.

In the binary image of FIG. 9, the pattern recognition software has also applied an edge detection process. In edge detection, meaningful objects in the image are singled out by comparing each point to the surrounding points. A point which is black (on) and has a white (off) adjacent point is determined to be an edge point. Edge points remain black (on) and non-edge points are made white (off).

Continuing to refer to FIG. 9, the binary image 74 after edge detection has wide lines which are difficult to analyze. Wide lines result in more points to process and require more computer resources. In addition, the shape of features in the image is more difficult to detect by computer when the lines are broad.

Figure 10:
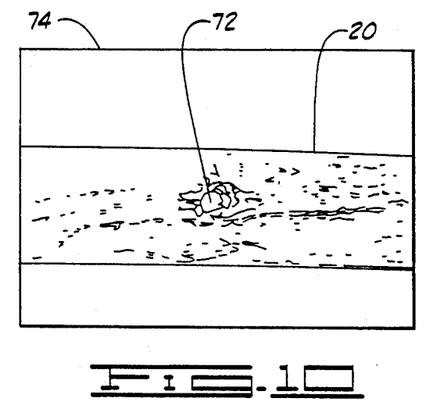
FIG. 10 is a diagram of the image frame of FIG. 9 after the application of skeleton thinning by the computer system.

In order to overcome the difficulties presented by wideline binary images, the pattern recognition software applies a skeletal thinning algorithm to narrow the edge lines. The result of the thinning process is shown in FIG. 10. By thinning the edge lines, the pattern recognition software reduces the data to be processed by the computer system 14 and highlights the shape of the edges.

After the edges have been thinned, the knot recognition software 36 removes horizontal line segments from the computer image 74. Because knots are generally elliptical in shape on the surface of a log, the components of the edge of a knot are typically curved or diagonal in the computer image 74. Most noise (non-knot) edges, such as wood grain and wood splits, are horizontal lines.

Figure 11:
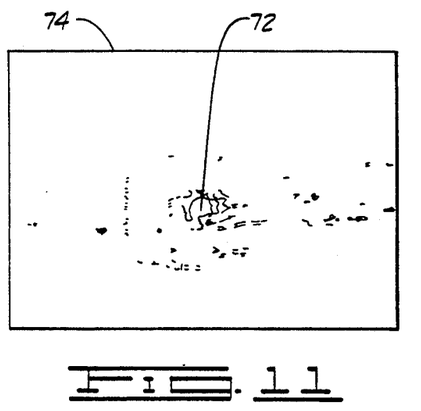
FIG. 11 is a diagram of the image frame of FIG. 10 after removal of isolated edge lines by the computer system.

Referring to FIG. 11, the knot recognition software 36 has removed horizontal line segments from the binary image 74. Although it is undesirable to remove horizontal lines which form a part of a knot, loss of such data does not present any major problems in the pattern recognition processes which follow.

After edge detection, thinning and removal of horizontal lines, the pattern recognition software removes remaining isolated edge lines and isolated points. A knot region contains a grouping of edges and any isolated lines and points are determined to be non-knot areas.

Finally, the surface knot pattern recognition phase is performed. The pattern recognition software searches the binary image of the log surface for curved edges and long diagonal edge lines. Various combinations of left or right curve edges and diagonal edge lines indicate possible knot regions. For example, a grouped pair of left and right curve edges is often the location of a knot. A left or right curve edge opposing a diagonal edge line is also a potential knot region.

Next, histograms of the diagonal lines are generated and analyzed to determine the knot regions. A large number of dark pixels or points is indicative of a knot region. A region must have points defining at least one half of an ellipse that fits within the region in order to qualify as a knot region.

Figure 12:
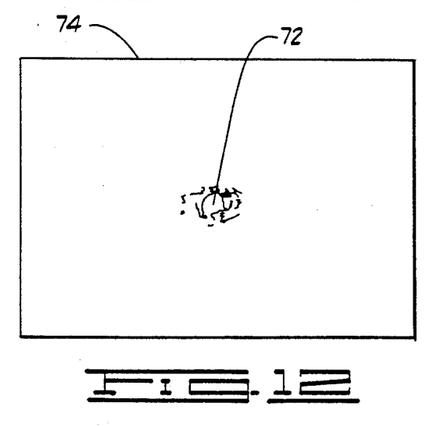
FIG. 12 is a diagram of the image frame of FIG. 11 after the knot region is located by the computer system.

With reference to FIG. 12, the knot 72 is shown in the binary image 74 after the pattern recognition software has identified it as a knot region. The knot surface diameter $d_k$ of the knot 72 may be scaled from the dimensions of the knot region in the computer image 74. The knot angular location $\alpha_k$ is also determined from the computer image 74. It is simply equal to the log angular location $\alpha_L$ for the image frame in which the knot is detected by pattern recognition.

Computer Model and Knot Geometry

Having located the knot regions, the computer system 14 may generate a computer model of the log and its knots. A grid coordinate system is used to identify the location and size of the various knots in the log 20.

Figure 13:
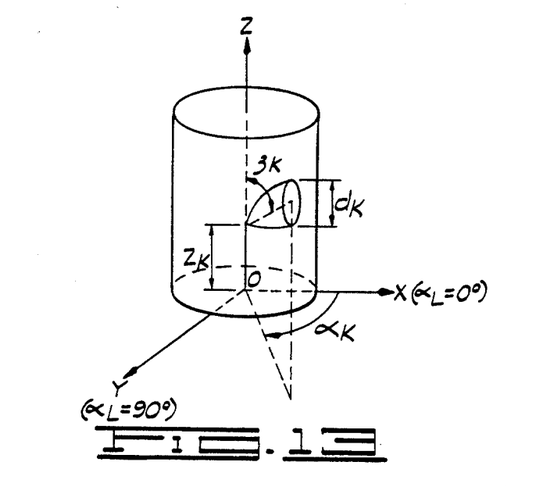
FIG. 13 is a diagram illustrating the coordinate system and geometry of the computer model of the log.

With reference now to FIG. 13, the computer system 14 utilizes an o-x-y-z coordinate system with the origin (o) at the center of the bottom end of the log and the z-axis extending along the longitudinal center-line of the log 20. The positive x-axis is arbitrarily defined to be the initial orientation of the log 20 ($\alpha_L=0$). Continuing the rotation, the positive y-axis corresponds to $\alpha_L=90°$, the negative x-axis corresponds to $\alpha_L=180°$, and the negative y-axis corresponds to $\alpha_L=270°$.

In order to describe the features of a knot, the following parameters are defined with reference to FIG. 13.

The knot angular location, denoted by $\alpha_k$, is the angular location of a knot with respect to the reference line $\overline{oz}$, or the positive x-axis.

The knot longitudinal location, designated as $z_k$, is the distance along the line $\overline{oz}$ between the pitch of the knot and the origin o.

Knot angular displacement, denoted by $\beta_k$, is the angle between the centerline of a knot and the centerline (z-axis) of the log.

Knot surface diameter, denoted by $d_k$, is the diameter of a knot at the log surface.

Three of the four knot features, therefore, are derived from the log profile for a lump knot. The fourth parameter, $\beta_k$, relates to the internal geometry of a knot and cannot be determined by scanning the surface of the log. The value of $\beta_k$, therefore, is determined by a statistical study of knots occurring in southern pine logs. Actual values for $\beta_k$ were measured from cross-sectional cuts or X-rays of a sample logs. The mean of the $\beta_k$ angles measured was 49.82° with a standard deviation of 5.34°. Accordingly, $\beta_k=50°$ is used for modeling the geometry of all knots. Although this assumption for $\beta_k$ does introduce some degree of inaccuracy, comparisons of actual and model features indicate that the effect of the assumed $\beta_k$ value on the final log orientation and sawing pattern is insignificant.

Once surface knot recognition is complete, the knot features $\alpha_k$, $d_s$ and $z_k$ are readily available from the x-y-z grid-coordinate model of the log. The 50° $\beta_k$-angle is applied to the surface knots as it was to the lump knots to define the internal geometry of the surface knots. Therefore, after the knot recognition and geometry procedures are performed, the computer model of the log is complete with both surface and internal characteristics of all knots detected in the log from the optical scan.

Centerline Knots and Edge Knots

Figure 14:
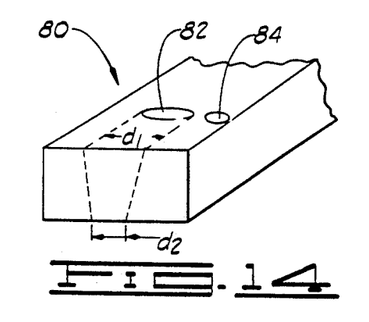
FIG. 14 is a diagram illustrating a centerline knot and an edge knot on the wide face of a board.

Referring now to FIG. 14, a portion of a board 80 with two knots 82 and 84 on the wide face of the board 80. Knot 82 is a centerline knot because it is located at the centerline of the wide face of the board 80. Similarly, knot 84 is called an edge knot because it appears at the edge of the wide face of the board 80.

Continuing to refer to FIG. 14, the centerline knot 82 has two diameters, $d_1$ and $d_2$, appearing on the upper and lower wide faces of the board 80, respectively. For purposes of grading the board 80, the knot face size $d_f$ is defined to be the average of these two diameters.

$$d_f = \frac{d_1 + d_2}{2}$$

The knot face size $d_f$ for an edge knot, such as edge knot 84 is determined by the same equation. It should be understood that if the knot only appears on one face of the board 80, then either $d_1$ or $d_2$ is equal to zero.

Figure 15:
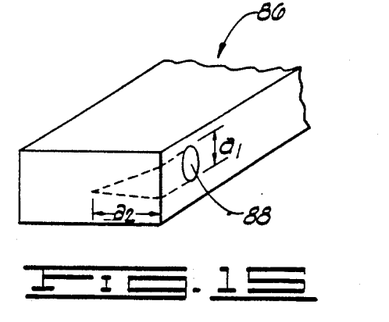
FIG. 15 is a diagram illustrating a knot on the narrow face of a board.

Turning now to FIG. 15, a portion of a board 86 with a knot 88 on the narrow face of the board 86 is illustrated. For purposes of grading a board with this type of knot 88, the knot face area, denoted by $A_f$, is determined by the following equation.

$$A_f = \frac{a_1 \times a_2}{2}$$

where $a_1$ is the diameter of the knot on the narrow face $a_2$ is the depth of the knot into the board.

The knot face area $A_f$ is then used to compute the knot ratio $r_k$ according to the equation which follows.

$$r_k = \frac{A_f}{A_c}$$

where $A_c$ is the area of the end of the board.

The values for knot face size $d_f$ and knot ratio $r_k$ are used in determining the grade of a board in a manner which is described hereafter.

Selecting a Sawing Pattern and Log Orientation

Figure 16:
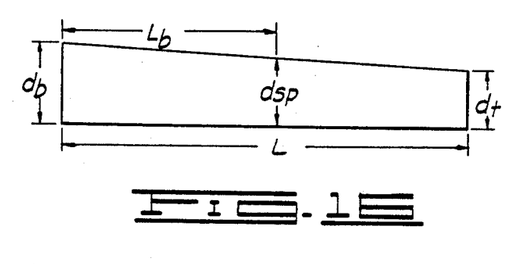
FIG. 16 is a diagram showing the parameters for determining the set point diameter of a log.

As shown in FIG. 16, each log has a length L, a bottom diameter $d_b$, a top diameter $d_t$, and a set point diameter $d_{sp}$. The volume yield of a log depends upon the sawing pattern selected for a log. A factor used in selecting a sawing pattern is the set point diameter, which is defined by the following equation.

$$d_{sp} = d_b - \frac{96(d_b - d_t)}{1}$$

Figure 17:
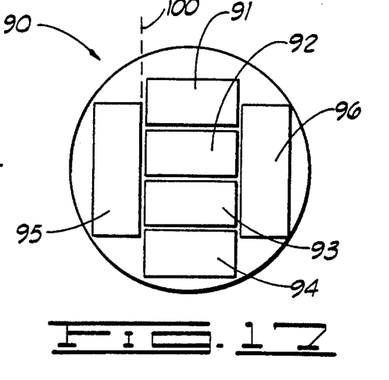
FIG. 17 is a diagram illustrating a typical sawing pattern suitable for a log with a set point diameter of approximately nine inches.

With reference now to FIG. 17, a suitable sawing pattern 90 for a log with a 9-inch $d_{sp}$ is described. In this sawing pattern, four 2×4 boards and two 2×6 boards are cut. The four 2×4 boards are indicated by reference numerals 91, 92, 93 and 94. Reference numbers 95 and 96 designate the two 2×6 boards.

Continuing to refer to FIG. 17, the broken line 100 indicates the log orientation angle $\alpha_L$ for the initial cut of the sawing pattern. In other words, the intersection of the line 100 with the outer surface of the log corresponds to $\alpha_L$ for that particular log orientation. In this way, the relationship between the sawing pattern 90 and the grid coordinates of the log and knots computer model is established.

After a sawing pattern is selected, the software "cuts" the computer model of the log into boards according to the selected sawing pattern. All of the knots are then located on the resulting boards. The sizes and locations of the knots on each board determine the quality of the board. A grade from 1 to 4 is assigned to each knot on each board according to the size and location of the knot. Grade 1 is the highest quality and grade 4 is the lowest quality. Basic knot-related lumber grading rules are applied to determine the grade of the board. Tables 1a and 1b illustrate the lumber grading rules which are applied to knots on the wide face side of the board. Table 1a applies to centerline knots and Table 1b applies to edge knots.

TABLE 1a

| | Grading Centerline Knots | |
|---|---|---|
| Size | Knot Face Size | Grade |
| 2" × 4" | $d_f <= 1\frac{1}{2}"$ | 1 |
| | $1\frac{1}{2}" < d_f <= 2"$ | 2 |
| | $2" < d_f <= 2\frac{1}{2}"$ | 3 |
| | $d_f > 2\frac{1}{2}"$ | 4 |
| 2" × 6" | $d_f <= 2\frac{1}{4}"$ | 1 |
| | $2\frac{1}{4}" < d_f <= 2\frac{7}{8}"$ | 2 |
| | $2\frac{7}{8}" < d_f <= 3\frac{1}{8}"$ | 3 |
| | $d_f > 3\frac{1}{8}"$ | 4 |
| 2" × 8" | $d_f <= 2\frac{7}{8}"$ | 1 |
| | $2\frac{7}{8}" < d_f <= 3\frac{1}{2}"$ | 2 |
| | $3\frac{1}{2}" < d_f <= 4\frac{1}{2}"$ | 3 |
| | $d_f > 4\frac{1}{2}"$ | 4 |

TABLE 1b

| | Grading Edge Knots | |
|---|---|---|
| Size | Knot Face Size | Grade |
| 2" × 4" | $d_f <= 1"$ | 1 |
| | $1" < d_f <= 1\frac{1}{4}"$ | 2 |
| | $1\frac{1}{4}" < d_f <= 1\frac{3}{4}"$ | 3 |
| | $d_f > 1\frac{3}{4}"$ | 4 |
| 2" × 6" | $d_f <= 1\frac{1}{2}"$ | 1 |
| | $1\frac{1}{2}" < d_f <= 1\frac{7}{8}"$ | 2 |
| | $1\frac{7}{8}" < d_f <= 2\frac{1}{8}"$ | 3 |
| | $d_f > 2\frac{1}{8}"$ | 4 |
| 2" × 8" | $d_f <= 2"$ | 1 |
| | $2" < d_f <= 2\frac{1}{2}"$ | 2 |
| | $2\frac{1}{2}" < d_f <= 3\frac{1}{2}"$ | 3 |
| | $d_f > 3\frac{1}{2}"$ | 4 |

In the case of a knot which is neither a centerline nor an edge knot, the size of the knot is linearly enlarged to that of a centerline knot and grading for centerline knots is used.

For knots which appear on the narrow-face side of a board, the grade of the board is determined by the knot ratio $r_k$ according to Table 2.

TABLE 2

| Grading Narrow-Face Knots | |
|---|---|
| Knot Ratio Range | Grade |
| $r_k <= \frac{1}{4}"$ | 1 |
| $\frac{1}{4}" < r_k <= \frac{3}{8}"$ | 2 |
| $\frac{3}{8}" < r_k <= \frac{1}{2}"$ | 3 |
| $r_k > \frac{1}{2}"$ | 4 |

A board rarely contains only a single knot. In the usual case of multiple knots on a board, the board is assigned the lowest of the grades received from all the knots on the board.

After each board which would be cut from the selected sawing pattern is assigned a grade, the value yield of each board is calculated. Table 3 illustrates a typical set of dollar values for various sizes and grades of boards.

TABLE 3

| | Prices of 1,000 Board Feet by Grade | | | |
|---|---|---|---|---|
| Size of Board | Grade of Board | | | |
| | 1 | 2 | 3 | 4 |
| 2" × 4" | $242 | $210 | $185 | $140 |
| 2" × 6" | $230 | $210 | $170 | $120 |
| 2" × 8" | $280 | $210 | $165 | $120 |
| 1" × 4" | $550 | $380 | $230 | $195 |

The value yield of each board (VYB) is calculated according to the following equation.

$$VYB = P_g \times \frac{L_b \times A_c}{12 \times 1000}$$

where $P_g$ is the price of one thousand board feet of grade g boards from Table 3, $L_b$ is the length of the board in feet, and $A_c$ is the area of the end of the board in square inches as previously defined.

The value yield of the entire log is obtained simply by summing the value yields of all the boards cut from the log according to the selected sawing pattern. This log value yield is the result from one sawing pattern and one angle of log orientation ($\alpha_L=0°$).

The value yield software 40 then increases angle $\alpha_L$ by 1° and repeats the knot-related grading, the value yield of boards calculation and the value yield of the log computation. The angle $\alpha_L$ is incremented by 1° and grading/value yield computations are repeated until value yield results are computed for 360 log orientations, i.e. for $\alpha_L=0°$ to $\alpha_L=359°$.

With reference now to FIG. 18, the value yield of a log for the 360 log orientations is illustrated. A value yield in dollars is graphed versus the cutting angle, $\alpha_L$. The next step performed by the value yield software 40 is to select a log orientation or cutting angle from the information shown in FIG. 18.

In making the cutting angle selection, the value yield software 40 requires that the orientation selected has a width of high yields to ensure that the saw will hit the target area and not strike an adjacent valley. As shown in FIG. 18, there are two peaks in value yields. One peak occurs through the range of 168° to 174° and the other occurs at 330°. The value yield software, therefore, selects the center of the wider peak, $\alpha_L=171°$, as the optimal angle for sawing the log.

The preceeding discussion describes the selection of an optimal cutting angle for one sawing pattern. The present invention may be extended to analyze a number of sawing patterns. Then an optimal sawing pattern may be selected as well as a log orientation angle for sawing.

With reference now to FIG. 19, another sawing pattern 102 is described. The sawing pattern 102 is suitable for a 9-inch set point diameter and yields four 2×6 boards and two 2×4 boards. The four 2×6 boards are designated by reference numerals 104, 105, 106 and 107. The two 2×4 boards are indicated by reference numbers 108 and 109. The log orientation for the initial cut for the sawing pattern 102 is designated by broken line 120.

The value yield software 40 may be executed for the sawing pattern 102 as it was for sawing pattern 90 to "saw" the computer model of the log, grade the resulting boards, and calculate a value yield for 360 orientations of the log. After determining an optimal value yield for the two sawing patterns 90 and 102, the sawing pattern with the higher value yield is selected as an optimal sawing pattern.

It should be understood that the computer sawing, grading, value yield calculations and log orientation selection may be repeated for any number of sawing patterns. Once the computer model of the log and its knots is created, the analysis of various sawing patterns may be performed by the computer system 14 with ease.

An additional benefit of the present invention relates to the grading of lumber. Typically, grading of boards cut from a log is largely accomplished by manual inspection of the boards. Some of this grading work may be accomplished by the computer system 14.

By identifying each board with its assigned grade in the computer system 14, it may not be necessary to manually inspect every board in order to assign a grade to it. The manual effort in grading lumber may be reduced to spot inspections to verify the accuracy of the computer grading.

Changes may be made in the combinations, operations and arrangements of the various parts and elements described herein without departing form the spirit and scope of the invention as defined in the following claims.

What is claimed is:

1. An apparatus for determining location, size and shape of knots in a log to be cut into lumber products, the apparatus comprising:
   a log holder adapted to display the surface of a log to be cut into boards;
   a light source adapted to illuminate the log;
   a camera positioned to produce optical images of the surface of the log;
   a computer connected to the camera and adapted to receive the optical images of the surface of the log from the camera; and
   computer means, operable within the computer, for creating from the optical images of the outer surface of the log a three-dimensional computer model of the log with locations, sizes and shapes of knots in the log.

2. The apparatus of claim 1 further comprising:
   a background material positioned between the log and the log holder to provide visual contrast in the optical images between the log and the background material.

3. The apparatus of claim 2 wherein the camera is a color, charge-coupled device video camera.

4. The apparatus of claim 3 wherein the background material is a material of uniform color selected from the group consisting of red material, green material and blue material.

5. The apparatus of claim 1 wherein the computer means further comprises:
   image processing means for producing computer images of the log from the optical images of the camera;
   a three-dimensional computer model of the log;
   knot recognition means for identifying the location and size of knots on the surface of the log from the computer images of the log;
   knot geometry means for inserting the location, size and shape of knots in the log into the computer model of the log; and
   value yield means for using the computer model to simulate boards cut from the log according to a predetermined sawing pattern and log orientation and for determining an economic value of the simulated boards.

6. The apparatus of claim 5 wherein the knot recognition means further comprises:
   profile recognition means for identifying the location and size of each knot protruding from the surface of the log from the computer images showing the knot in profile; and
   pattern recognition means for identifying the location and size of each knot by analyzing shapes appearing in the computer images of the log.

7. The apparatus of claim 6 wherein the pattern recognition means further comprises:
   means for finding edges of shapes appearing in the computer images of the log;
   means for thinning the edges of shapes appearing in the computer images of the log;
   means for removing horizontal lines from the computer images of the log;
   means for removing isolated points and isolated lines from the computer images of the log; and means for identifying the location and size of knots by searching for curved and diagonal edges in the computer images.

8. The apparatus of claim 1 further comprising:
means for rotating the log about the longitudinal axis thereof; and
means for moving the camera parallel with the log to expose sections of the log in length-wise sequence to the camera in order to create optical images corresponding to each section of the log.

9. The apparatus of claim 8 wherein the sections of the log are uniform in length.

10. The apparatus of claim 9 wherein the optical image of each section of the log overlaps the optical image of the preceding optical image by a predetermined amount of overlap.

11. A method of determining an optimal log orientation and sawing pattern for cutting a log into boards, the steps of the method comprising:
 (a) scanning the log with a camera to produce a plurality of optical images of the surface of a log;
 (b) converting the optical images into computer images of the surface of the log;
 (c) recognizing the location of knots in the computer images of the surface of the log;
 (d) providing a computer model of the log;
 (e) modeling the geometry of each recognized knot inside the log from the appearance of the knot in the computer images of the surface of the log;
 (g) using the computer model to simulate a plurality of boards cut from the log according to a predetermined sawing pattern and for a plurality of log orientations;
 (h) analyzing the size and location of knots appearing on each simulated board;
 (i) assigning a grade and a corresponding economic value to each simulated board;
 (j) totaling the economic value of all the simulated boards cut from the log according to the predetermined sawing pattern for each log orientation; and
 (k) determining an optimal log orientation to obtain a high total economic value for the boards to be cut from the log according to the predetermined sawing pattern.

12. The method of claim 11 further comprising:
repeating steps (g) through (k) for a plurality of predetermined sawing patterns; and
determining an optimal predetermined sawing pattern from the plurality of sawing patterns to obtain a high total economic value for the boards to be cut from the log.

13. The method of claim 11 wherein step (a) further comprises:
beginning at a first end of the log;
establishing an initial orientation and direction of rotation for the log;
positioning a camera to frame the log one section at a time to produce optical images of the surface of the log, the log sections having equal widths; and
rotating the log in equal increments to obtain optical images of the log surface for each incremental log orientation within each log section.

14. The method of claim 11 wherein step (c) further comprises:
recognizing knots protruding from the surface of the log by analyzing the computer images of the log sections in profile; and
recognizing knots appearing on the surface of the log by analyzing patterns in the computer images of the log sections.

15. The method of claim 14 wherein the step of recognizing knots appearing on the surface of the log further comprises:
detecting edge lines in the computer images of each log section;
thinning the edge lines in the computer images of each log section;
removing horizontal lines from the computer images of each log section;
removing isolated lines and points from the computer images of each log section; and
analyzing the computer images of each log section for pairs of curved lines and pairs of diagonal lines as indications of the presence of a knot.

16. The method of claim 11 wherein step (i) further comprises:
determining the size of centerline knots on each simulated board;
determining the size of edge knots on each simulated board;
determining the size of knots appearing on the narrow face of each simulated board; and
assigning a grade to each simulated board from predetermined rules for grading boards by type and size of knots and the size of centerline knots, edge knots and narrow face knots on each simulated board.

17. The method of claim 16 further comprising:
determining an economic value for each simulated board according to a predetermined value versus grade table and the grade assigned to each simulated board.

* * * * *